US011857533B2

(12) United States Patent
Seo et al.

(10) Patent No.: US 11,857,533 B2
(45) Date of Patent: Jan. 2, 2024

(54) COMPOSITION FOR PREVENTING OR TREATING OBESITY OR LIPID-RELATED METABOLIC DISORDERS

(71) Applicant: Nexyon Biotech Co., Ltd., Seoul (KR)

(72) Inventors: Jung Taek Seo, Seoul (KR); Seok Jun Moon, Seoul (KR); Sung-Jin Kim, Seoul (KR)

(73) Assignee: Nexyon Biotech Co., Ltd., Seoul (KR)

( * ) Notice: Subject to any disclaimer, the term of this patent is extended or adjusted under 35 U.S.C. 154(b) by 0 days.

(21) Appl. No.: 17/055,058

(22) PCT Filed: Mar. 2, 2020

(86) PCT No.: PCT/KR2020/002958
§ 371 (c)(1),
(2) Date: Nov. 12, 2020

(87) PCT Pub. No.: WO2020/184884
PCT Pub. Date: Sep. 17, 2020

(65) Prior Publication Data
US 2021/0393581 A1    Dec. 23, 2021

(30) Foreign Application Priority Data
Mar. 13, 2019    (KR) ........................ 10-2019-0028547

(51) Int. Cl.
  *A61K 31/37* (2006.01)
  *A61P 1/16* (2006.01)
  *A61P 3/04* (2006.01)
  *A61P 3/10* (2006.01)
  *A61K 31/404* (2006.01)
  *A61K 31/473* (2006.01)
  *A61K 31/5377* (2006.01)
  *A61K 31/56* (2006.01)
  *A61K 31/568* (2006.01)
  *A61K 31/5685* (2006.01)
  *A61K 31/662* (2006.01)

(52) U.S. Cl.
  CPC ............ *A61K 31/37* (2013.01); *A61K 31/404* (2013.01); *A61K 31/473* (2013.01); *A61K 31/5377* (2013.01); *A61K 31/56* (2013.01); *A61K 31/568* (2013.01); *A61K 31/5685* (2013.01); *A61K 31/662* (2013.01); *A61P 1/16* (2018.01); *A61P 3/04* (2018.01); *A61P 3/10* (2018.01)

(58) Field of Classification Search
  CPC ............... A61K 31/37; A61P 1/16; A61P 3/04
  See application file for complete search history.

(56) References Cited

U.S. PATENT DOCUMENTS

2016/0361244 A1    12/2016    Munoz Ruiz et al.

FOREIGN PATENT DOCUMENTS

KR    10-20140090696    7/2014

OTHER PUBLICATIONS

Anbar et al. (Expert Opinion on Therapeutic Patents (2021) 31:453-472). (Year: 2021).*
Cecchi et al., "Carbonic anhydrase inhibitors: Inhibition of the human isozymes I, II, VA, and IX with a library of substituted difluoromethanesulfonamides," Bioorganic & Medicinal Chemistry Letters 15 (2005) 5192-5196.
Jiang et al., "Hepatic Overexpression of Steroid Sulfatase Ameliorates Mouse Models of Obesity and Type 2 Diabetes through Sex-specific Mechanisms," The Journal of Biological Chemistry, vol. 289, No. 12, pp. 8086-8097, Mar. 21, 2014.
Kim et al., "Effect of Whole Powder and Extracts of Gastrodiae Rhizoma on Serum lipids and Body Fat in Rats Fed High-Fat Diet," korean J. Food Sci. Technol, vol. 35, No. 4, pp. 720-725 (2003).
Jong Ho Lee, "Treatment of Obesity," Journal of Korean Society for Study of Obesity, vol. 1, No. 1, 1992, pp. 21-24.
Edward A. Lew, "Mortality and Weight: Insured Lives and the American Cancer Society Studies," Anals of Internal Medicine, Dec. 1985, vol. 103, No. 6 (Part 2), pp. 1024-1029.
Christos S. Mantzoros, "The Role of Leptin in Human Obesity and Disease: A Review of Current Evidence," Ann Intern Med., 1999, 130:671-680.
Matsuzawa et al., "Molecular Mechanism of Metabolic Syndrome X: Conribution of Adipocytokines Adipocyte-derived Bioactive Substances," Annals New York Academy of Sciences, pp. 146-154.
Mi Jung Park, "Recent Advances in Regulating Energy Homeostasis and Obesity," Korean Journal of Pediatrics, vol. 48, No. 2, 2005, pp. 126-137.
Roemmich and Rogol, "Hormonal Changes During Puberty and Their Relationship to Fat Distribution," American Journal of Human Biology, 11:209-224 (1999).
Alan R. Saltiel, "You are what you secrete," Aug. 2001, Nature Medicine, vol. 7, No. 8, pp. 887-888.
Winum et al., "Therapeutic applications of sulfamates," Expert Opin. Ther. Patents (2004) 14(9), pp. 1273-1308.
International Search Report dated Jun. 9, 2020 for International Application No. PCT/KR2020/002958, 5 pages.
L.W. Lawrence Woo et al., "Development of steroid sulfatase inhibitors," Molecular and Cellular Endocrinology, 340, 175-185 (2011).

* cited by examiner

*Primary Examiner* — Marcos L Sznaidman
(74) *Attorney, Agent, or Firm* — McDonnell Boehnen Hulbert & Berghoff LLP

(57) ABSTRACT

The present disclosure relates to a functional composition for the prevention, amelioration or treatment of obesity or lipid-related metabolic disorders, which comprises a steroid sulfatase inhibitor as an active ingredient.

4 Claims, 8 Drawing Sheets

Irosustat vehicle

Irosustat vehicle

Irosustat

COMPOSITION FOR PREVENTING OR TREATING OBESITY OR LIPID-RELATED METABOLIC DISORDERS

This application is a U.S. national phase application of International Patent Application no. PCT/KR2020/002958, filed Mar. 2, 2020, which claims the benefit of priority of Korean Patent Application no. 10-2019-0028547, filed Mar. 13, 2019.

TECHNICAL FIELD

The present disclosure relates to a functional composition for the prevention, amelioration or treatment of obesity or lipid-related metabolic disease.

BACKGROUND ART

In recent years, in Korea, as dietary life has become westernized along with economic growth, the amount of calories consumed has increased, and thus the obese population has also increased. Specifically, according to Ministry of Health and Welfare Statistical Yearbook 2013, the proportion of obese persons among adults over the age of 19 was 31.4%, which increased by 0.5% from 30.9% surveyed in 2010, and the childhood obesity rate has also increased rapidly.

Obesity by itself causes discomfort in life due to weight gain and body fattening, but the bigger problem of obesity is that obesity raises blood lipid levels, causes arteriosclerosis and heart diseases, increases insulin resistance, causing complications such as diabetes, menstrual irregularities and cancer, and causes chronic adult diseases such as hyperlipidemia, hypertension, coronary artery, and stroke. For this reason, treatment and prevention of obesity is essential (Lee J H, J. Kor. Soc. Obes., 1:21-24, 1992; Lew E A, Ann. Intern. Med., 103:1024-1029, 1985; Kim K I et al., Korean J. Food Sci. Technol., 35:720-725, 2003).

Obesity is known to be caused by genetic influences, environmental influences due to westernized dietary life, psychological influences due to stress, and the like, but the exact cause or mechanism of obesity is not clearly yet identified.

In the past, adipocytes have been recognized as cells that act to simply store excess energy in the human body in the form of triglycerides and to buffer external shocks. However, in recent years, adipocytes have been recognized as an endocrine organ that secretes adipocytokines, which regulate fasting, metabolism, and insulin sensitivity. Specifically, adipocytokines such as adiponectin, leptin, resistin, tumor necrosis factor alpha (TNF-α), and interleukin-6 (IL-6), are known to play an important role in maintaining homeostasis and regulating energy metabolism (Matsuzawa, Y. et al., Ann. Ny. Acad. Sci., 892:146-154, 1999; Saltiel, A. R., Nat. Med., 7:887-888, 2001).

In particular, since the leptin produced by the obesity gene is proportional to the amount of adipocytes, the serum leptin concentrations of obese people are shown to be higher than those of normal-weight people, and leptin is produced more in subcutaneous fat than in visceral fat. This leptin plays an important role in obesity in view of leptin secretion from adipocytes, and it acts not only on regulation of food intake, but also on energy consumption and reproductive function, suppresses appetite, and increases heat production through the sympathetic nervous system. In addition, leptin is a substance which suppresses appetite by acting on receptors in the hypothalamus while circulating through the brain, and is secreted by the brain when body fat increases. Furthermore, leptin was found to be one of substances that suppress appetite by stimulating the satiety center that controls satiety in the brain (Mantzoros, C. S., Ann Intern. Med., 130:671-680, 1999; Roemmich, J. N. and A. D., Am. J. Hum. Biol., 11:209-224, 1999).

The goals for treating obesity may be broadly divided into two. The first goal is to lose weight by burning excess fat, and the second goal is to improve metabolic imbalance. Currently, obesity treatment aims not only to lose weight, but also to improve metabolic abnormalities by removing factors that cause cardiovascular diseases early. In addition, studies have been actively conducted to suppress obesity through regulation of food intake and energy consumption. As organs that regulate food intake behavior, the hypothalamus and the motor nervous, autonomic nervous and peripheral nervous systems are all involved in the food intake behavior. In particular, the hypothalamus in the central nervous system plays an important role in the etiology of obesity, and neuropeptide Y, POMC/CART, melanocortin receptors, norepinephrine, and serotonin are representative factors which are secreted from the hypothalamus. Current strategies for developing obesity therapeutic agents include reducing food intake, inhibiting calorie absorption, promoting exothermic reactions, regulating energy metabolism, and controlling signaling through the nervous system (Park Mi-Jung, Korean J Pediatr 48(2), 2005).

Obesity therapeutic agents known to date are largely divided, according to their mechanism of action, into satiety stimulants, fat absorption inhibitors, and antipsychotic appetite suppressants. The most representative drugs for obesity treatment include Xenical™ (Roche Pharmaceuticals, Switzerland), Reductil™ (Abbott, USA), and Exolise™ (Arkopharma, France), but these drugs has problems in that they cause fatty stool, intestinal gas generation, abdominal bloating, fecal incontinence, etc., and have adverse effects such as heart diseases, respiratory diseases, and nervous system diseases, and the persistence of the efficacy thereof is low.

DISCLOSURE

Technical Problem

An object of the present disclosure is to provide a functional composition capable of effectively preventing, ameliorating or treating obesity.

Another object of the present disclosure is to provide a functional composition capable of effectively preventing, ameliorating or treating lipid-related metabolic disease.

Still another object of the present disclosure is to a method for the prevention, amelioration or treatment of obesity.

Yet another object of the present disclosure is to a method for the prevention, amelioration or treatment of lipid-related metabolic disease.

However, the technical objects to be achieved by the present disclosure are not limited to the aforementioned technical objects, and other technical objects which are not mentioned herein will be clearly understood by those skilled in the art, to which the present disclosure pertains, from the following description.

Technical Solution

One embodiment of the present disclosure is directed to a composition for the prevention, amelioration or treatment of obesity, the composition comprising a steroid sulfatase inhibitor as an active ingredient.

In the present disclosure, the "steroid sulfatase" functions to regulate the local production of estrogens and androgens from precursors in several tissues. This enzyme catalyzes the hydrolysis of the sulfate ester groups of 3-hydroxy steroids, which are inactive transport or precursor forms of the active 3-hydroxy steroids. In the present disclosure, the "steroid sulfatase inhibitor" functions to block the local production of the estrogens and androgens.

In the present disclosure, the steroid sulfatase inhibitor may be one or more selected from the group consisting of irosustat, 2-(hydroxyphenyl)indole sulfate, 5-androstene-3,17-diol-3 sulfate, estrone-3-O-methylthiophosphonate (E1-3-MTP), estrone-3-O-sulfamate (EMAIL), 4-methylcoumarin 7-O-sulfamate (COUMA1E), KW-2581, STX213, and morpholino. For example, the steroid sulfatase inhibitor may be, but is not limited to, irosustat.

In the present disclosure, irosustat may have a structure represented by the following Formula 1, the IUPAC name of irosustat may be (6-oxo-8,9,10,11-tetrahydro-7H-cyclohepta[c]chromen-3-yl) sulfamate, and irosustat may be available under CAS No. 288628-05-7:

[Formula 1]

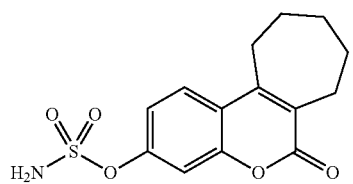

The composition which is provided by the present disclosure may comprise a pharmaceutically acceptable salt form of the steroid sulfatase inhibitor, for example, irosustat. The pharmaceutically acceptable salt should have low toxicity to the human body and should not 10 adversely affect the biological activity and physicochemical properties of the parent compound. The pharmaceutically acceptable salt may be, but is not limited to, an acid addition salt of the steroid sulfatase inhibitor, preferably an irosustat compound, formed by a pharmaceutically acceptable free acid.

Preferred salt forms of the compound according to the present disclosure include salts with 15 inorganic or organic acids. In this case, the inorganic acids include hydrochloric acid, sulfuric acid, nitric acid, phosphoric acid, perchloric acid, bromic acid, and the like. In addition, the organic acids include acetic acid, methanesulfonic acid, ethanesulfonic acid, p-toluenesulfonic acid, fumaric acid, maleic acid, malonic acid, phthalic acid, succinic acid, lactic acid, citric acid, gluconic acid, tartaric acid, salicylic acid, malic acid, oxalic acid, benzoic acid, embonic acid, aspartic acid, glutamic acid, and the like. Organic bases that may be used to prepare organic base addition salts include tris(hydroxymethyl)methylamine, dicyclohexylamine, etc. Amino acids that may be used to prepare amino acid addition salts include natural amino acids such as alanine and glycine. It will be obvious to those skilled in the art to which the present disclosure pertains that acids or bases other than the above-exemplified inorganic acids, organic acids, organic bases and amino acids may be used.

In the present disclosure, the salt form may be prepared by a conventional method. For example, the salt form may be prepared by dissolving the steroid sulfatase inhibitor, for example, irosustat, in a water-miscible solvent such as methanol, ethanol, acetone or 1,4-dioxane, and then adding a free acid or a free base to the solution, followed by crystallization.

Meanwhile, a hydrate or solvate form of the steroid sulfatase inhibitor, for example, irosustat, may also be included in the scope of the compounds according to the present disclosure.

In the present disclosure, the "obesity" may mean a condition or disease with excessive body fat caused by energy imbalance.

Another embodiment of the present disclosure is directed to a composition for the prevention, amelioration or treatment of lipid-related metabolic disease, the composition comprising a steroid sulfatase inhibitor as an active ingredient.

In the present disclosure, the steroid sulfatase inhibitor may be one or more selected from the group consisting of irosustat, 2-(hydroxyphenyl)indole sulfate, 5-androstene-3,17-diol-3 sulfate, estrone-3-O-methylthiophosphonate, estrone-3-O-sulfamate, 4-methylcoumarin 7-O-sulfamate, KW-2581, STX213, and morpholino. For example, the steroid sulfatase inhibitor may be, but is not limited to, irosustat.

The composition which is provided by the present disclosure may comprise a pharmaceutically acceptable salt form of the steroid sulfatase inhibitor, for example, irosustat. The pharmaceutically acceptable salt should have low toxicity to the human body and should not adversely affect the biological activity and physicochemical properties of the parent compound. The pharmaceutically acceptable salt may be, but is not limited to, an acid addition salt of the steroid sulfatase inhibitor, preferably an irosustat compound, formed by a pharmaceutically acceptable free acid.

Preferred salt forms of the compound according to the present disclosure include salts with inorganic or organic acids. In this case, the inorganic acids include hydrochloric acid, sulfuric acid, nitric acid, phosphoric acid, perchloric acid, bromic acid, and the like. In addition, the organic acids include acetic acid, methanesulfonic acid, ethanesulfonic acid, p-toluenesulfonic acid, fumaric acid, maleic acid, malonic acid, phthalic acid, succinic acid, lactic acid, citric acid, gluconic acid, tartaric acid, salicylic acid, malic acid, oxalic acid, benzoic acid, embonic acid, aspartic acid, glutamic acid, and the like. Organic bases that may be used to prepare organic base addition salts include tris(hydroxymethyl)methylamine, dicyclohexylamine, etc. Amino acids that may be used to prepare amino acid addition salts include natural amino acids such as alanine and glycine. It will be obvious to those skilled in the art to which the present disclosure pertains that acids or bases other than the above-exemplified inorganic acids, organic acids, organic bases and amino acids may be used.

In the present disclosure, the salt form may be prepared by a conventional method. For example, the salt form may be prepared by dissolving the steroid sulfatase inhibitor, for example, irosustat, in a water-miscible solvent such as methanol, ethanol, acetone or 1,4-dioxane, and then adding a free acid or a free base to the solution, followed by crystallization.

Meanwhile, hydrate or solvate form of the steroid sulfatase inhibitor, for example, irosustat, may also be included in the scope of the compounds according to the present disclosure.

In the present disclosure, the "lipid-related metabolic disease" refers to a disease caused by excessive accumulation of lipids in a living body. In the present disclosure, a specific example of the lipid-related metabolic disease may be selected from the group consisting of diabetes, hyperlipidemia, hepatic steatosis, hepatitis, liver cirrhosis, arteriosclerosis, hypertension, cardiovascular disease, and metabolic syndromes in which the above diseases occur simultaneously.

The composition for the prevention, amelioration or treatment of obesity and the composition for the prevention, amelioration or treatment of lipid-related metabolic disease, which are provided by the present disclosure, may be each used as a pharmaceutical composition or a food composition, but are not limited thereto.

In the present disclosure, the "prevention" may include, without limitation, all actions capable of blocking symptoms caused by obesity or lipid-related metabolic disease, suppressing or delaying the symptoms using the composition of the present disclosure.

In the present disclosure, the "treatment" and "amelioration" may include, without limitation, all actions capable of alleviating or beneficially changing symptoms caused by obesity or lipid-related metabolic disease using the composition of the present disclosure.

In the present disclosure, the pharmaceutical composition may be in the form of capsule, tablet, granule, injection, ointment, powder or beverage, and the pharmaceutical composition may be for administration to humans.

For use, the pharmaceutical composition of the present disclosure may be formulated in the form of, but not limited to, oral preparations, such as powders, granules, capsules, tablets, and aqueous suspensions, as well as external preparations, suppositories, and sterile injectable solutions, according to the respective conventional methods. The pharmaceutical composition of the present disclosure may comprise pharmaceutically acceptable carriers. Pharmaceutically acceptable carriers that may be used for oral administration include binders, lubricants, disintegrants, excipients, solubilizers, dispersants, stabilizers, suspending agents, pigments, flavorings, and the like, and pharmaceutically acceptable carriers that may be used for injection include buffers, preservatives, analgesics, solubilizers, isotonic agents, stabilizers, and the like. Pharmaceutically acceptable carriers that may be used for topical administration include bases, excipients, lubricants, preservatives, and the like. The formulation of the pharmaceutical composition of the present disclosure may be prepared in various ways by mixing with pharmaceutically acceptable carriers as described above.

For example, for oral administration, the pharmaceutical composition may be prepared in the form of tablets, troches, capsules, elixirs, suspensions, syrups, or wafers, and for injection, the pharmaceutical composition may be presented in unit dose ampoules or multi-dose containers. In addition, the pharmaceutical composition may be formulated as solutions, suspensions, tablets, capsules, sustained-release formulations, or the like.

Meanwhile, examples of carriers, excipients and diluents suitable for formulation include lactose, dextrose, sucrose, sorbitol, mannitol, xylitol, erythritol, maltitol, starch, gum acacia, alginate, gelatin, calcium phosphate, calcium silicate, cellulose, methyl cellulose, microcrystalline cellulose, polyvinyl pyrrolidone, water, methylhydroxy benzoate, propylhydroxy benzoate, talc, magnesium stearate, and mineral oil. In addition, the pharmaceutical composition of the present disclosure may further comprise a filler, an anticoagulant, a lubricant, a wetting agent, a flavoring agent, an emulsifier, a preservative, etc.

The routes of administration of the pharmaceutical composition according to the present disclosure include, but are not limited to, oral, intravenous, intramuscular, intra-arterial, intramedullary, intradural, intracardiac, transdermal, subcutaneous, intraperitoneal, intranasal, gastrointestinal, topical, sublingual and intrarectal routes. Oral or parenteral administration is preferred.

In the present disclosure, "parenteral" includes subcutaneous, transdermal, intravenous, intramuscular, intra-articular, intra-synovial, intrasternal, intradural, intra-lesional and intra-cranial injection or infusion techniques. The pharmaceutical composition of the present disclosure may also be formulated as suppositories for intrarectal administration.

The pharmaceutical composition of the present disclosure may vary depending on various factors, including the activity of a specific compound used, the patient's age, body weight, general health, sex and diet, the time of administration, the route of administration, excretion rate, the drug content, and the severity of a specific disease to be prevented or treated. The dose of the pharmaceutical composition may vary depending on the patient's condition and body weight, the severity of the disease, the form of drug, and the route and period of administration, but may be suitably selected by a person skilled in the art and may be 0.0001 to 50 mg/kg/day or 0.001 to 50 mg/kg/day. The pharmaceutical composition may be administered once or several times a day. The dose is not intended to limit the scope of the present disclosure in any way. The pharmaceutical composition according to the present disclosure may be formulated as pills, sugar-coated tablets, capsules, liquids, gels, syrups, slurries, or suspensions.

The food composition comprising the composition of the present disclosure as an active ingredient may be prepared as various foods, for example, beverages, gums, teas, vitamin complexes, powders, granules, tablets, capsules, confectionery, cakes, bread and the like. The food composition of the present disclosure comprises a plant extract having almost no toxicity and side effects, and thus may be used with an easy mind even when it is administered for a long period of time for preventive purposes.

When the composition of the present disclosure is comprised in the food composition, it may be added in an amount of 0.1 to 50 wt % based on the total weight.

When the food composition is prepared as a beverage, there is no particular limitation, except that the beverage comprises the food composition at the indicated percentage. The beverage may comprise, as additional ingredients, various flavorings or natural carbohydrates, like conventional beverages. Examples of the natural carbohydrates include monosaccharides such as glucose, disaccharides such as fructose, polysaccharides such as sucrose, conventional sugars such as dextrin and cyclodextrin, and sugar alcohols such as xylitol, sorbitol, and erythritol. Examples of the flavorings include natural flavorings (thaumatin, *stevia* extracts, such as rebaudioside A and glycyrrhizin, etc.) and synthetic flavorings (saccharin, aspartame, etc.).

In addition, the food composition of the present disclosure may comprise various nutrients, vitamins, minerals (electrolytes), flavorings such as synthetic flavorings and natural flavorings, colorants, pectic acid and its salt, alginic acid and its salt, organic acids, protective colloidal thickeners, pH adjusting agents, stabilizers, preservatives, glycerin, alcohol, carbonizing agents as used in carbonated beverages, etc.

Such components may be used individually or in combination. Although the proportion of such additives is not of great importance, it is generally selected within a range of 0.1 to about 50 parts by weight based on 100 parts by weight of the composition of the present disclosure.

Still another embodiment of the present disclosure is directed to a method for the prevention or treatment of obesity, the method including administering a pharmaceutically effective amount of a steroid sulfatase inhibitor to a subject.

In the present disclosure, the "steroid sulfatase" functions to regulate the local production of estrogens and androgens from precursors in several tissues. This enzyme catalyzes the hydrolysis of the sulfate ester groups of 3-hydroxy steroids, which are inactive transport or precursor forms of the active 3-hydroxy steroids. In the present disclosure, the "steroid sulfatase inhibitor" functions to block the local production of the estrogens and androgens.

In the present disclosure, the steroid sulfatase inhibitor may be one or more selected from the group consisting of irosustat, 2-(hydroxyphenyl)indole sulfate, 5-androstene-3, 17-diol-3 sulfate, estrone-3-O-methylthiophosphonate, estrone-3-O-sulfamate, 4-methylcoumarin 7-O-sulfamate, KW-2581, STX213, and morpholino. For example, the steroid sulfatase inhibitor may be, but is not limited to, irosustat.

One embodiment of the present disclosure provides a method for the prevention or treatment of obesity, the method including a step of administering, to a subject, a pharmaceutically effective amount of a compound represented by the following Formula 1 or a pharmaceutically acceptable salt thereof.

[Formula 1]

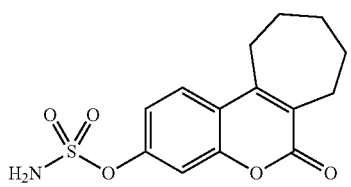

In the present disclosure, the "subject" refers to a subject in need of the prevention or treatment of obesity, and may include not only primates such as humans, but also mammals such as cattle, horses, sheep, pigs, goats, camels, antelopes, dogs, and cats, but is not limited thereto.

In the present disclosure, "administering" means a process of introducing the active ingredient of the present disclosure into a subject by any suitable method. In the treatment method of the present disclosure, the active ingredient may be administered through various routes such as oral or parenteral routes.

For the purpose of the present disclosure, a specific pharmaceutically effective amount for a particular patient is preferably applied differently depending on various factors, including the kind and degree of response to be achieved, whether the composition comprising the active ingredient comprises other agents in some cases, the patient's age, weight, health conditions, sex and diet, the time of administration, the route of administration, the excretion rate of the composition comprising the active ingredient, the duration of treatment, and other drugs used in combination with or simultaneously with the specific composition, and similar factors well known in the medical field.

The method for the prevention or treatment of obesity according to the present disclosure may be, but is not limited to, a combination therapy further including administering a compound or substance having therapeutic activity against one or more diseases.

In the present disclosure, the "combination" is to be understood to refer to simultaneous, separate or sequential administration. Where the administration is sequential or separate, the delay in administering the second component should not be such as to lose the beneficial effect of the combination.

In the prevention or treatment method of the present disclosure, the contents related to Formula 1, obesity, irosustat, preferred salt forms, prevention, treatment, and the like, overlap with those described above, and thus the description thereof will be omitted herein in order to avoid excessive complexity of the specification.

Yet another embodiment of the present disclosure is directed to a method for the prevention or treatment of lipid-related metabolic disease, the method including a step of administering a pharmaceutically effective amount of a steroid sulfatase inhibitor to a subject.

In the present disclosure, the "steroid sulfatase" functions to regulate the local production of estrogens and androgens from precursors in several tissues. This enzyme catalyzes the hydrolysis of the sulfate ester groups of 3-hydroxy steroids, which are inactive transport or precursor forms of the active 3-hydroxy steroids. In the present disclosure, the "steroid sulfatase inhibitor" functions to block the local production of the estrogens and androgens.

In the present disclosure, the steroid sulfatase inhibitor may be one or more selected from the group consisting of irosustat, 2-(hydroxyphenyl)indole sulfate, 5-androstene-3, 17-diol-3 sulfate, estrone-3-O-methylthiophosphonate, estrone-3-O-sulfamate, 4-methylcoumarin 7-O-sulfamate, KW-2581, STX213, and morpholino. For example, the steroid sulfatase inhibitor may be, but is not limited to, irosustat.

One embodiment of the present disclosure provides a method for the prevention or treatment of lipid-related metabolic disease, the method including a step of administering, to a subject, a pharmaceutically effective amount of a compound represented by the following Formula 1 or a pharmaceutically acceptable salt thereof:

[Formula 1]

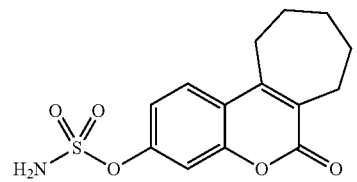

In the prevention or treatment method of the present disclosure, the contents related to Formula 1, lipid-related metabolic disease, irosustat, pharmaceutically acceptable salt thereof, prevention, treatment, subject, administration, combination and the like, overlap with those described above, and thus the description thereof will be omitted herein in order to avoid excessive complexity of the specification.

Advantageous Effects

The composition which is provided by the present disclosure may effectively prevent, ameliorate or treat obesity by lowering the body fat content and reducing the size of adipocytes.

In addition, the composition which is provided by the present disclosure may also effectively prevent, ameliorate or treat lipid-related metabolic disease by ameliorating hepatic steatosis, increasing glucose/insulin sensitivity and lowering blood cholesterol or triglyceride levels.

BEST MODE

One embodiment of the present disclosure is directed to a composition for the prevention, amelioration or treatment of obesity, the composition comprising a steroid sulfatase inhibitor as an active ingredient.

Another embodiment of the present disclosure is directed to a composition for the prevention, amelioration or treatment of lipid-related metabolic disease, the composition comprising a steroid sulfatase inhibitor as an active ingredient.

Still another embodiment of the present disclosure is directed to a method for the prevention or treatment of obesity, the method including administering a pharmaceutically effective amount of a steroid sulfatase inhibitor to a subject.

Yet another embodiment of the present disclosure is directed to a method for the prevention or treatment of lipid-related metabolic disease, the method including administering a pharmaceutically effective amount of a steroid sulfatase inhibitor to a subject.

MODE FOR INVENTION

Hereinafter, the present disclosure will be described in more detail with reference to examples. It will be obvious to those skilled in the art that these examples are merely to describe the present disclosure in more detail and the scope of the present disclosure according to the subject matter of the present disclosure is not limited by these examples.

Examples

[Preparation Example 1] Preparation of Irosustat

The compound (6-oxo-8,9,10,11-tetrahydro-7H-cyclohepta[c]chromen-3-yl) sulfamate (hereinafter referred to as "irosustat") represented by the following Formula 1 was purchased and prepared:

[Formula 1]

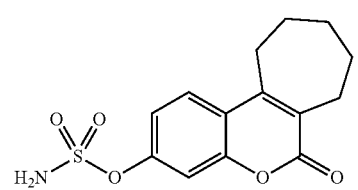

[Experimental Example 1] Weight Loss Effect in High-Fat-Diet-Induced Obesity Mouse Model 8-week-old C57BL/6 mice were fed with a 60% high-fat diet, and a vehicle or irosustat (10 mg/kg) prepared in Preparation Example 1 was administered orally to the mice once a day for a total of 10 days. The body weights of the mice were measured at the same time every week, and the results are graphically shown in FIG. 1.

Figure 1:
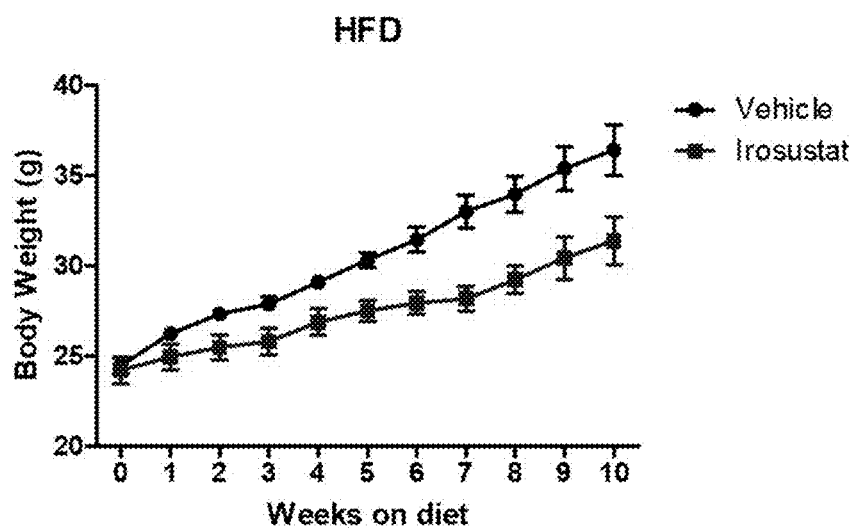
FIG. 1 graphically shows the results of measuring changes in mouse body weight after administering irosustat or a vehicle to a high-fat-diet-induced obesity mouse model in Experimental Example 1.

As shown in FIG. 1, it could be confirmed that the body weight of the control group to which the vehicle was administered was 36.4+/−3.4 g, whereas the body weight of the drug-administered group to which irosustat was administered was 31.4+/−5.0 g, suggesting that the body weight of the drug-administered group significantly decreased by about 14% compared to that of the control group.

Figure 2A:
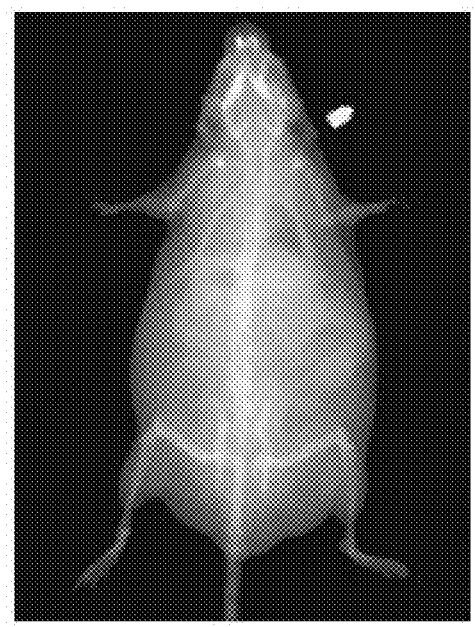
FIGS. 2A and 2B are X-ray images taken after administering irosustat (FIG. 2B) or a vehicle (FIG. 2A) to a high-fat-diet-induced obesity mouse model in Experimental Example 2.
Figure 2B:
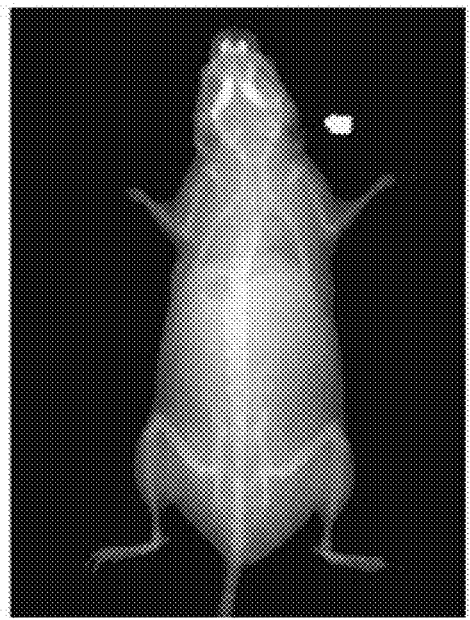

[Experimental Example 2] Fat Reduction Effect (1) in High-Fat-Diet-Induced Obesity Mouse Model An experiment was performed under the same conditions as in Experimental Example 1 above, except that the mice were imaged using DEXA (Dual-energy X-ray absorptiometry) after the vehicle or irosustat was administered orally to the mice for 13 weeks. The images are shown in FIGS. 2A and 2B. In addition, the fat masses and lean masses of the mice were measured, and the results are shown in FIG. 3.

Figure 3:
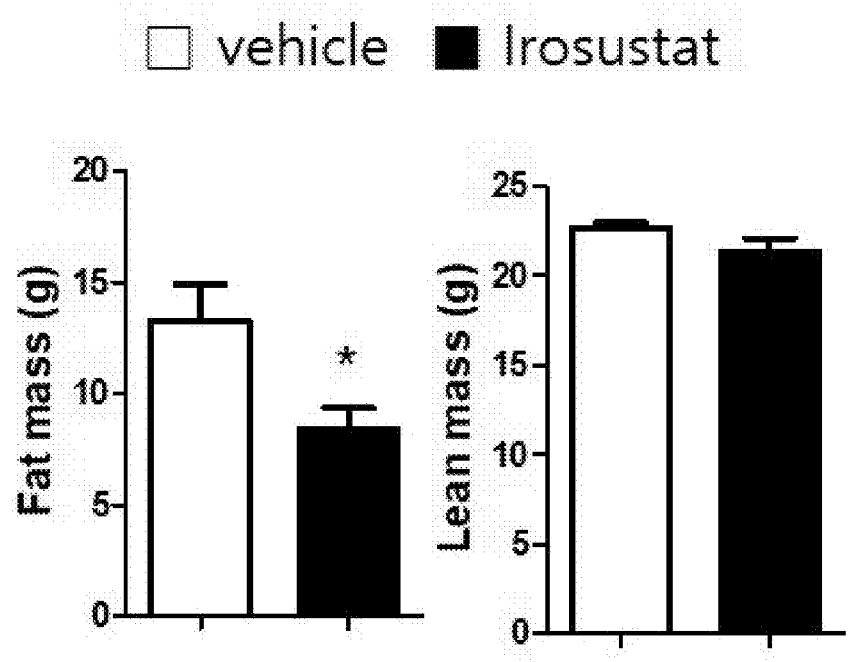
FIG. 3 graphically shows the results of measuring changes in mouse fat mass and lean mass after administering irosustat or a vehicle to a high-fat-diet-induced obesity mouse model in Experimental Example 2.

As shown in FIGS. 2A, 2B and 3, the fat mass of the drug-administered group to which irosustat was administered significantly decreased compared to that of the control group to which the vehicle was administered, but the body weight except fat, that is, lean mass, was similar between the two groups, suggesting that the mouse weight loss effect in Experimental Example 1 is attributable to fat reduction.

Figure 4A:
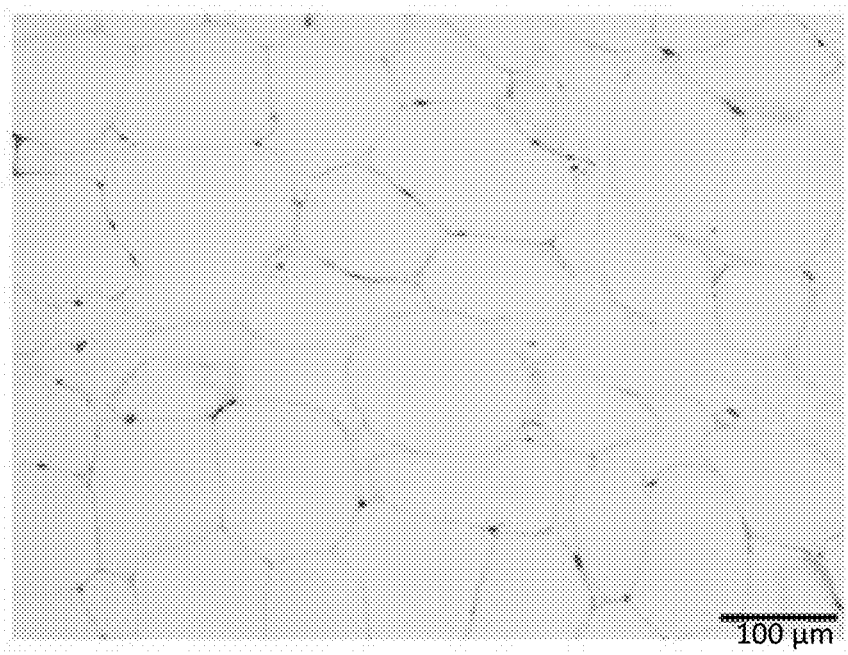
FIGS. 4A and 4B shows microscopic images of mouse abdominal fat tissue, taken after administering irosustat (FIG. 4B) or a vehicle (FIG. 4A) to a high-fat-diet-induced obesity mouse model in Experimental Example 3.
Figure 4B:
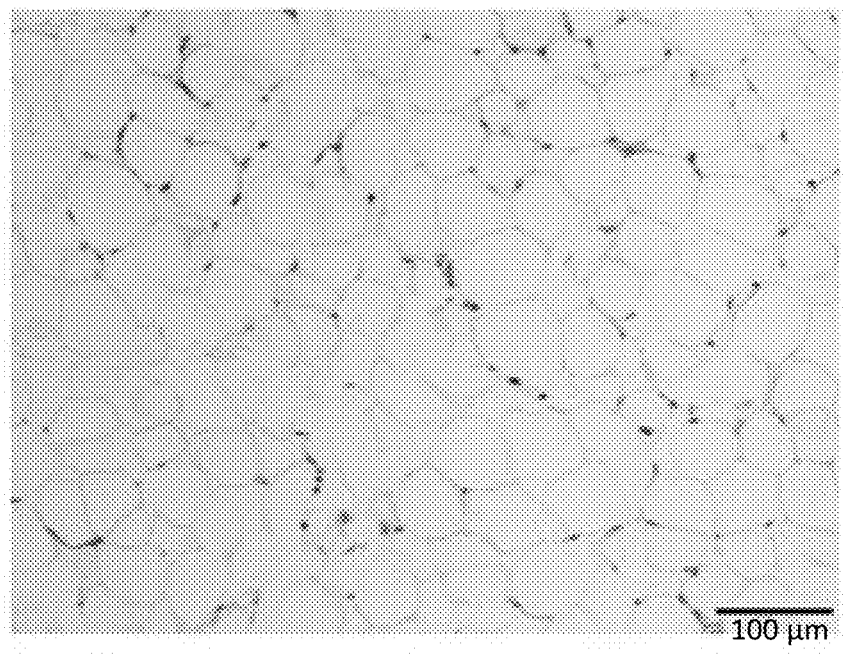

[Experimental Example 3] Fat Reduction Effect (2) in High-Fat-Diet-Induced Obesity Mouse Model An experiment was performed under the same conditions as in Experimental Example 1 above, except that the mice were euthanized after oral administration of irosustat for 13 weeks and abdominal fat tissue was taken and then imaged with a microscope. The images are shown in FIGS. 4A and 4B. In addition, the areas of adipocytes in the abdominal fat tissue in the control group and the drug-administered group were measured, and the results are shown in FIG. 5.

Figure 5:
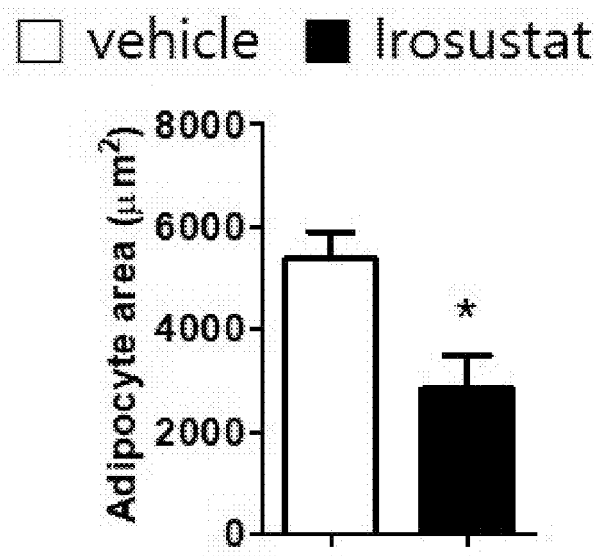
FIG. 5 graphically shows the results of measuring the size of mouse adipocytes after administering irosustat or a vehicle to a high-fat-diet-induced obesity mouse model in Experimental Example 3.

As shown in FIGS. 4A, 4B and 5, it could be confirmed that the size of adipocytes in the drug-administered group to which irosustat was administered significantly decreased compared to that in the control group to which the vehicle was administered.

[Experimental Example 4] Hepatic Steatosis Amelioration Effect in High-Fat-Diet-Induced Obesity Mouse Model An experiment was performed under the same conditions as in Experimental Example 1 above, except that the mice were euthanized after oral administration of irosustat for 13 weeks and hepatic tissue was taken and then imaged with a microscope. The images are shown in FIGS. 6A and 6B.

Figure 6A:
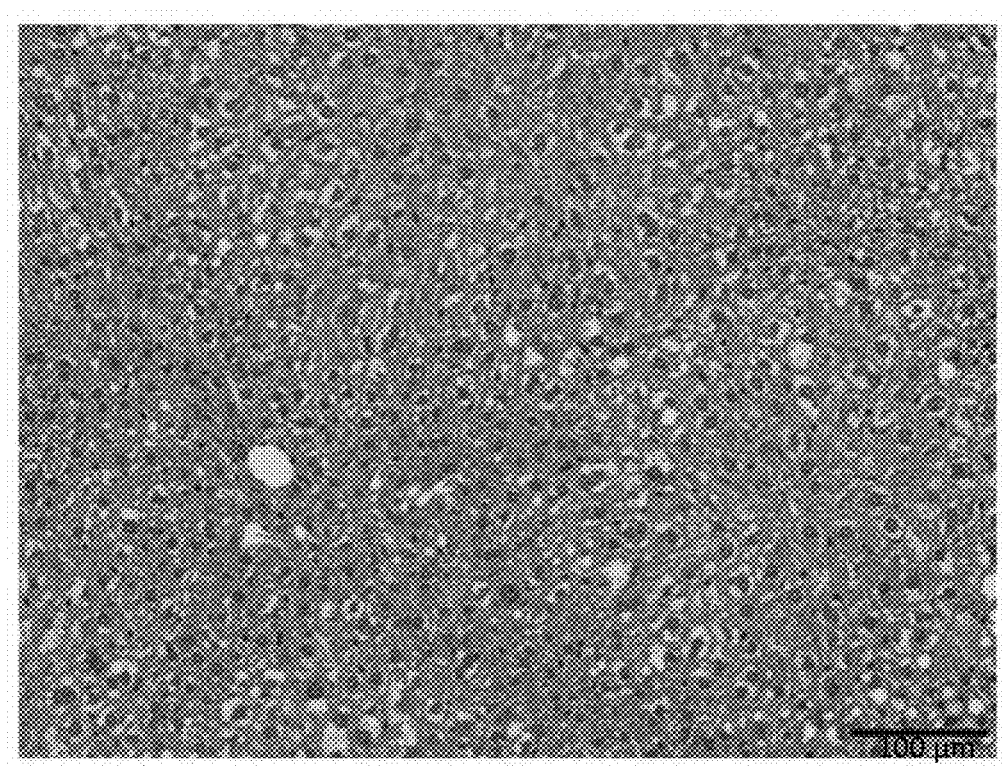
FIGS. 6A and 6B shows microscopic images of mouse liver tissue, taken after administering irosustat (FIG. 6B) or a vehicle (FIG. 6A) to a high-fat-diet-induced obesity mouse model in Experimental Example 4.
Figure 6B:
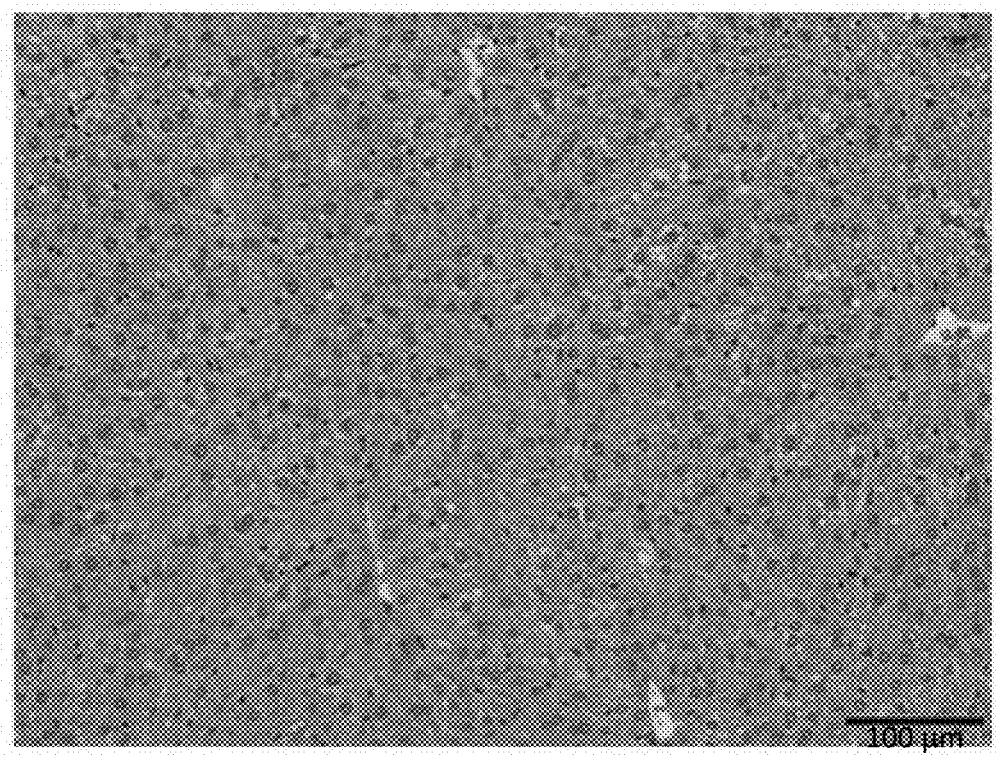

As shown in FIGS. 6A and 6B, it could be confirmed that the findings of hepatic steatosis caused by the high-fat diet in the drug-administered group to which irosustat was administered were significantly improved compared to those in the control group to which the vehicle was administered.

Figure 7:
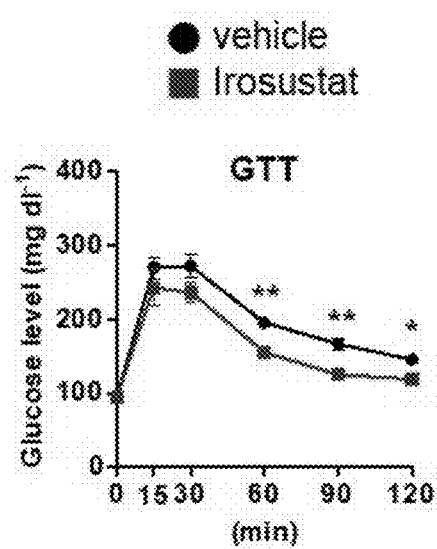
FIG. 7 graphically shows the results of measuring changes in blood glucose level after performing a glucose tolerance test following administration of irosustat or a vehicle to a high-fat-diet-induced obesity mouse model in Experimental Example 5.
Figure 8:
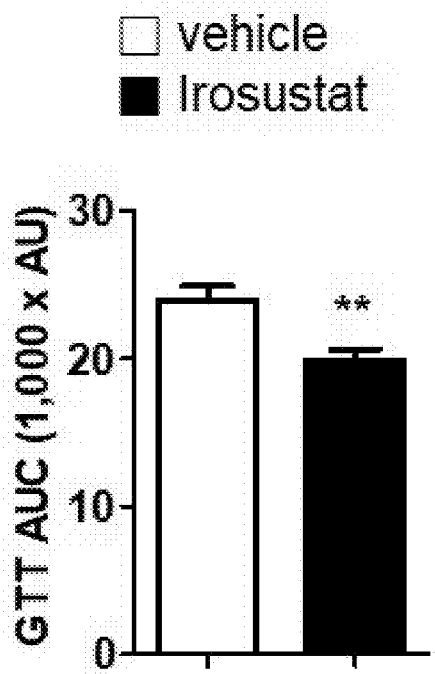
FIG. 8 graphically shows the results of measuring AUC (area under the glucose-time curve) after performing a glucose tolerance test following administration of irosustat or a vehicle to a high-fat-diet-induced obesity mouse model in Experimental Example 5.

[Example 5] Increase in Glucose/Insulin Sensitivity in High-Fat-Diet-Induced Obesity Mouse Model 1. Glucose tolerance test (GTT)
An experiment was performed under the same conditions as in Experimental Example 1 above, except that the mice were fasted for 16 hours after oral administration of irosustat for 11 weeks, and glucose was injected intraperitoneally into the mice at a dose of 1 g/kg body weight. 0 min, 15 min, 30 min, 60 min, 90 min and 120 min after intraperitoneal injection, blood was collected from the tail of each mice and the glucose level in the blood was measured. The results are shown in FIG. 7. However, during the glucose tolerance test, a stable environment was provided to the experimental animals. In addition, AUC (area under the glucose-time curve) was measured using the following Equation 1 and the results are shown in FIG. 8. In Equation 1, C0, C15, C30, C60, C90 and C120 are glucose levels measured at 0 min, 15 min, 30 min, 60 min, 90 min and 120 min, respectively.

$$AUC=0.5\times(0.5\times C0+C15+C30+C60+C90+0.5\times C120)$$ [Equation 1]

As shown in FIGS. 7 and 8, the blood glucose level in the drug-administered group to which irosustat was administered significantly decreased compared to that in the control group to which the vehicle was administered.

Figure 9:
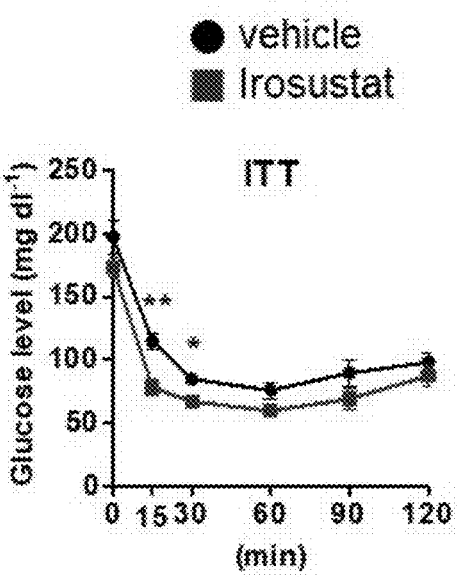
FIG. 9 graphically shows the results of measuring changes in blood glucose level after performing an insulin tolerance test (ITT) following administration of irosustat or a vehicle to a high-fat-diet-induced obesity mouse model in Experimental Example 5.

2. Insulin tolerance test (ITT)
An experiment was performed under the same conditions as in Experimental Example 1 above, except that the mice were fasted for 2 hours after oral administration of irosustat for 12 weeks, and then the blood glucose levels of the mice were measured and insulin was injected intraperitoneally into the mice at a dose of 0.8 units/kg body weight. 0 min, 15 min, 30 min, 60 min, 90 min and 120 min after intraperitoneal injection, blood was collected from the tail of each mice and the glucose level in the blood was measured. The results are shown in FIG. 9. In addition, AUC was measured using Equation 1 above and the results are shown in FIG. 10.

Figure 10:
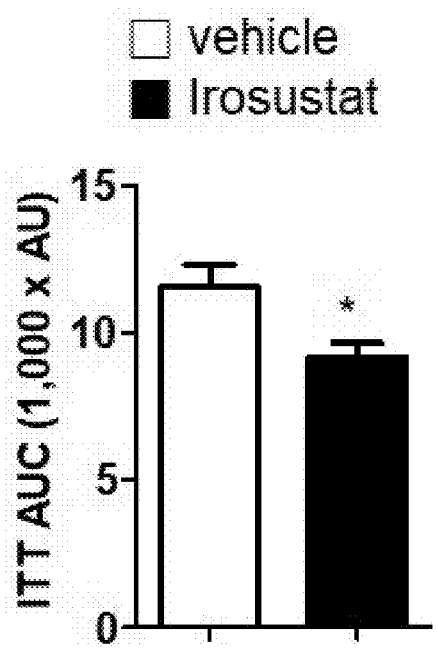
FIG. 10 graphically shows the results of measuring AUC (area under the glucose-time curve) after performing an insulin tolerance test following administration of irosustat or a vehicle to a high-fat-diet-induced obesity mouse model in Experimental Example 5.

As shown in FIGS. 9 and 10, it could be confirmed that the blood glucose level in the drug-administered group to which irosustat was administered significantly decreased compared to that in the control group to which the vehicle was administered.

[Experimental Example 6] Decreases in Blood Cholesterol and Triglyceride Levels in High-Fat-Diet-Induced Obesity Mouse Model An experiment was performed under the same conditions as in Experimental Example 1 above, except that the blood cholesterol and triglyceride levels in the control group and the drug-administered group were measured after oral administration of irosustat for 13 weeks. The results of measurement of the cholesterol and triglyceride levels are shown in FIGS. 11 and 12, respectively.

Figure 11:
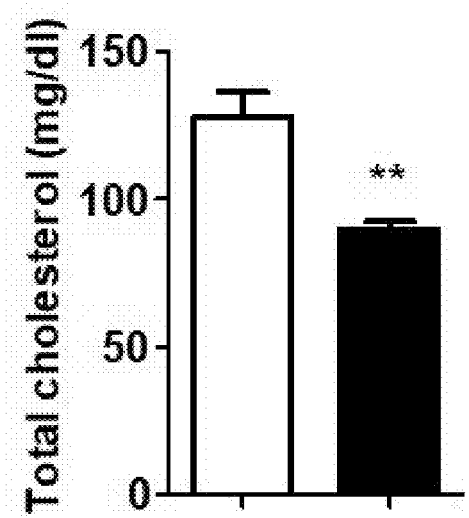
FIG. 11 graphically shows the results of measuring changes in blood cholesterol level after administering irosustat or a vehicle to a high-fat-diet-induced obesity mouse model in Experimental Example 6.
Figure 12:
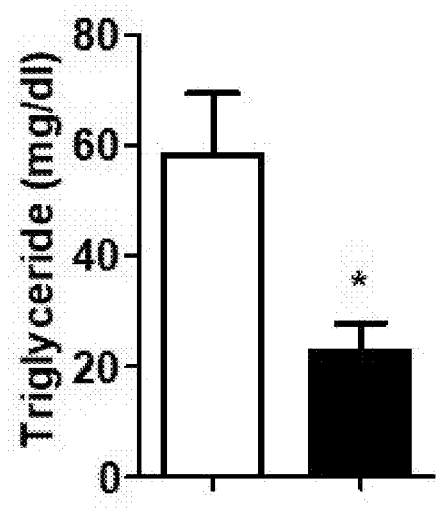
FIG. 12 graphically shows the results of measuring changes in blood triglyceride level after administering irosustat or a vehicle to a high-fat-diet-induced obesity mouse model in Experimental Example 6.

As shown in FIGS. 11 and 12, it could be confirmed that the blood cholesterol and triglyceride levels in the drug-administered group to which irosustat was administered significantly decreased compared to those in the control group to which the vehicle was administered.

Although the present disclosure has been described in detail based on the above results, it will be obvious to those skilled in the art to which the present disclosure pertains that the scope of the present disclosure is not limited thereto and various modifications and alterations are possible, without departing from the technical spirit of the present disclosure as described in the appended claims.

INDUSTRIAL APPLICABILITY

The composition which is provided by the present disclosure may effectively prevent, ameliorate or treat obesity by lowering the body fat content and reducing the size of adipocytes. In addition, the composition which is provided by the present disclosure may also effectively prevent, ameliorate or treat lipid-related metabolic disease by ameliorating hepatic steatosis, increasing glucose/insulin sensitivity and lowering blood cholesterol or triglyceride levels.

The invention claimed is:
1. A method for ameliorating or treating obesity, comprising administering a pharmaceutically effective amount of a pharmaceutical composition comprising irosustat to a subject.
2. The method of claim 1, wherein the pharmaceutical composition comprises a salt, hydrate or solvate form of the irosustat.
3. A method for ameliorating or treating lipid-related metabolic disease selected from the group consisting of diabetes, hyperlipidemia, hepatic steatosis, hepatitis, liver cirrhosis, arteriosclerosis, hypertension, cardiovascular disease, and metabolic syndromes in which the above diseases occur simultaneously, the method comprising administering a pharmaceutically effective amount of a pharmaceutical composition comprising irosustat to a subject.

4. The method of claim 3, wherein the pharmaceutical composition comprises a salt, hydrate or solvate form of the irosustat.

\* \* \* \* \*